United States Patent
Kobilka et al.

(10) Patent No.: US 11,655,153 B2
(45) Date of Patent: May 23, 2023

(54) EXTENDED ABSORBANCE SOLAR LEAF AND METHODS OF MAKING

(71) Applicant: International Business Machines Corporation, Armonk, NY (US)

(72) Inventors: Brandon M. Kobilka, Fishkill, NY (US); Jason T. Wertz, Pleasant Valley, NY (US); Joseph Kuczynski, North Port, FL (US); Scott B. King, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 753 days.

(21) Appl. No.: 16/659,172

(22) Filed: Oct. 21, 2019

(65) Prior Publication Data

US 2020/0048094 A1    Feb. 13, 2020

Related U.S. Application Data

(62) Division of application No. 15/848,743, filed on Dec. 20, 2017, now Pat. No. 10,526,205.

(51) Int. Cl.
| | |
|---|---|
| *C01B 32/194* | (2017.01) |
| *C07D 409/14* | (2006.01) |
| *H01L 31/0445* | (2014.01) |
| *H01L 31/0216* | (2014.01) |
| *C07D 257/08* | (2006.01) |
| *C07D 513/04* | (2006.01) |
| *C07D 517/04* | (2006.01) |
| *C07D 519/00* | (2006.01) |
| *H01L 51/00* | (2006.01) |
| *H01L 51/44* | (2006.01) |
| *H01G 9/20* | (2006.01) |

(52) U.S. Cl.
CPC .......... *C01B 32/194* (2017.08); *C07D 257/08* (2013.01); *C07D 409/14* (2013.01); *C07D 513/04* (2013.01); *C07D 517/04* (2013.01); *C07D 519/00* (2013.01); *H01L 31/02167* (2013.01); *H01L 31/0445* (2014.12); *H01L 51/0067* (2013.01); *H01L 51/0068* (2013.01); *H01L 51/0072* (2013.01); *C01B 2204/32* (2013.01); *H01G 9/2059* (2013.01); *H01L 51/0071* (2013.01); *H01L 51/0094* (2013.01); *H01L 51/447* (2013.01)

(58) Field of Classification Search
None
See application file for complete search history.

(56) References Cited

U.S. PATENT DOCUMENTS

| | | |
|---|---|---|
| 5,331,183 A | 7/1994 | Sariciftci et al. |
| 2013/0247989 A1 | 9/2013 | Bazan et al. |
| 2014/0034880 A1 | 2/2014 | Blouin et al. |
| 2014/0311559 A1 | 10/2014 | Lam et al. |
| 2015/0083206 A1 | 3/2015 | Novoselov et al. |
| 2017/0141318 A1 | 5/2017 | Campos et al. |
| 2019/0185326 A1 | 6/2019 | Kobilka et al. |

OTHER PUBLICATIONS

Tan, et al. Solution-Processed Rhenium Oxide: A Versatile Anode Buffer Layer for High Performance Polymer Solar Cells with Enhanced Light Harvest, Adv. Energy Mater.2014,4,1300884. pp. 1-7.
Qiao, et al. "Well Defined Nanographene-Rhenium Complex as an efficient Electrocatalyst and Photosatalyst for Selective CO2 Reduction," Journal of the American Chemical Society, Dec. 5, 2016.
Wang, et al. "Solution-Processed Organic Solar Cells with 9.8% Efficiency Based on a New Small Molecule Containing a 2D Fluorinated Benzodithiophene Central Unit," Adv. Electron. Mater. 2016, pp. 1-7.
Gim et al,"D-A-D-type narrow-bandgap small-molecule photovoltaic donors: pre-synthesis virtual screening using density functional theory," Phys. Chem. Chem. Phys., 2016, 18, 15054-15059.
Sun et al. "Solution-processed small-molecule solar cells with 6.7% efficiency," Published Online: Nov. 6, 2011, DOI: 10.1038/NMAT3160.
IBM, "List of IBM Patents or Patent Applications Treated as Related," for U.S. Appl. No. 16/659,172, filed Oct. 21, 2019, 2 pages.

*Primary Examiner* — Po-Chih Chen
(74) *Attorney, Agent, or Firm* — Patterson + Sheridan, LLP

(57) ABSTRACT

In an embodiment is provided a method of making a photo-absorbing composition that includes forming a donor-acceptor small molecule (DASM) by bonding an electron donor portion to an electron acceptor portion; and bonding the DASM to a nanographene structure using a Stille coupling reaction, a Suzuki cross-coupling reaction, or a C—H activation cross-coupling reaction. In another embodiment is provided films that include a photo-absorbing composition.

16 Claims, No Drawings

EXTENDED ABSORBANCE SOLAR LEAF AND METHODS OF MAKING

CROSS-REFERENCE TO RELATED APPLICATIONS

This application is a divisional of co-pending U.S. patent application Ser. No. 15/848,743, filed Dec. 20, 2017. The aforementioned related patent application is herein incorporated by reference in its entirety.

FIELD OF THE DISCLOSURE

The present disclosure relates generally to graphene-based solar absorbers. This disclosure relates to extending the absorbance spectrum of such absorbers by coupling other absorbing species to nanographene structures.

BACKGROUND

Existing solar conversion devices rely on chromophores to absorb solar radiation at the earth's surface and convert it to electrical or chemical energy. The bulk of the radiant solar energy is located in the IR and Visible portion of the electromagnetic spectrum. Most solar conversion devices tend to absorb in the blue region of the visible range, leaving a large portion of the solar spectrum unutilized. Such solar absorbers have poor conversion efficiency as a result. Consequently, methods and materials to extend the absorption spectrum of solar conversion and utilize more of the available solar energy in the red and infrared region of the solar spectrum is needed.

SUMMARY OF THE DISCLOSURE

In one aspect, a method of making a photo-absorbing composition is disclosed that includes forming a donor-acceptor small molecule (DASM) by bonding an electron donor portion selected from the group consisting of

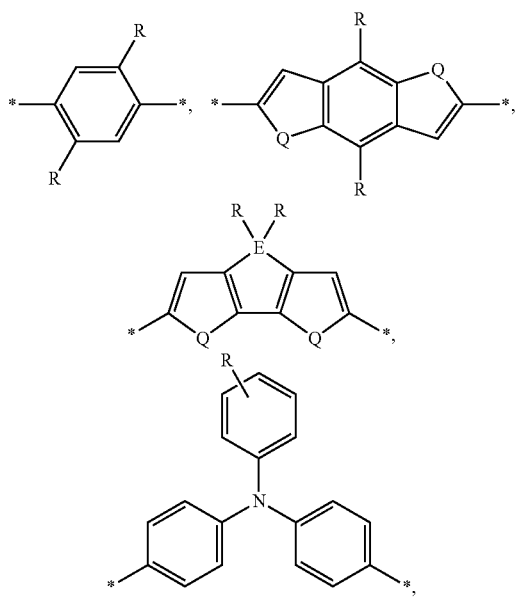

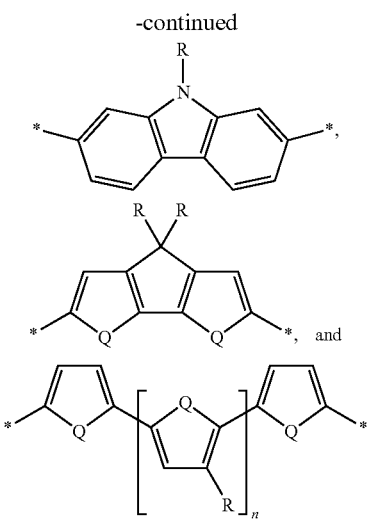

to an electron acceptor portion selected from the group consisting of

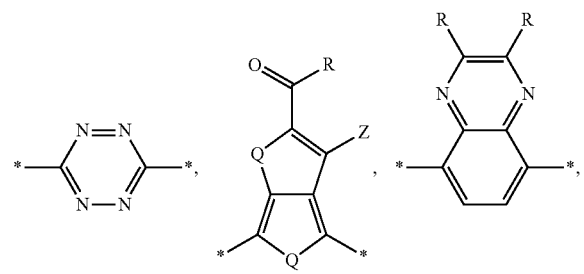

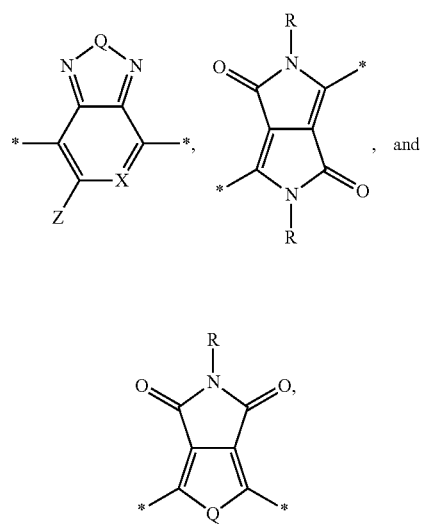

wherein the starred bonds are sites for bonding to other chemical structures; R is, independently in each instance, an alkyl, alkoxy, vinyl, aryl group, or fluorinated hydrocarbon group; Q is, independently in each instance, O, S, or Se; E is, independently in each instance, Si or Ge; Z is, independently in each instance, a proton or a fluorine atom; X is, independently in each instance, C or N; and bonding the DASM to a nanographene structure selected from the group consisting of

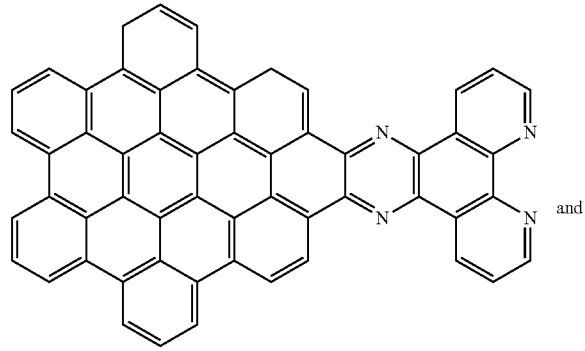

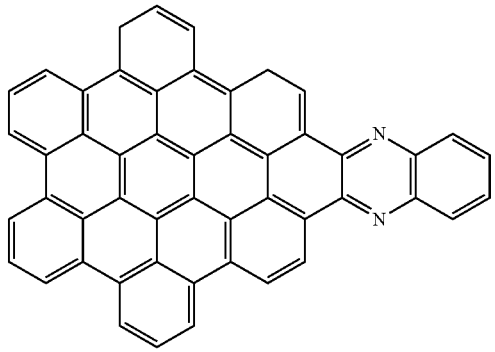

and using a Stille coupling reaction, a Suzuki cross-coupling reaction, or a C—H activation cross-coupling reaction.

In another aspect, a film is disclosed that includes a photo-absorbing composition having a structure from the group consisting of

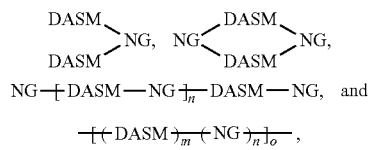

wherein DASM is a small molecule comprising one or more electron donor portions selected from the group consisting of

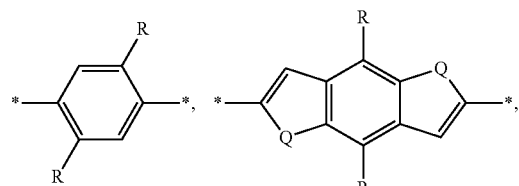

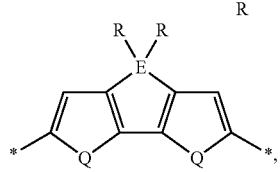

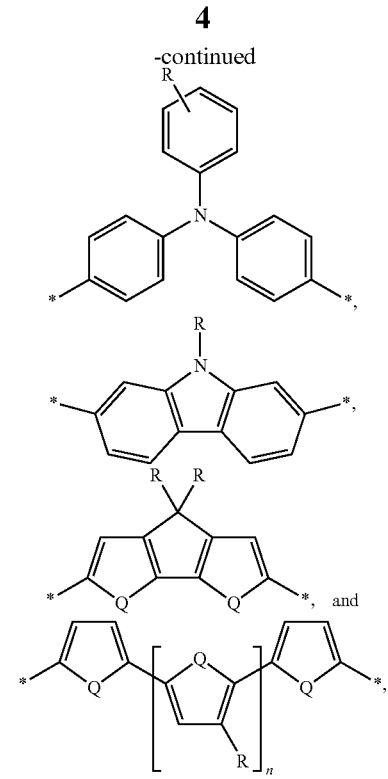

and one or more electron acceptor portions selected from the group consisting of

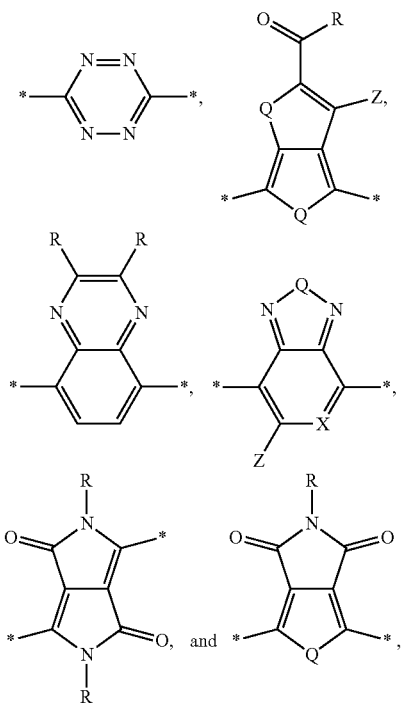

wherein the starred bonds are sites for bonding to other chemical structures; R is, independently in each instance, an alkyl, alkoxy, vinyl, aryl group, or fluorinated hydrocarbon group; Q is, independently in each instance, O, S, or Se; E is, independently in each instance, Si or Ge; Z is, independently in each instance, a proton or a fluorine atom; X is, independently in each instance, C or N; and m, n, and o are integers greater than or equal to 1; and wherein NG is a nanographene structure selected from the group consisting of

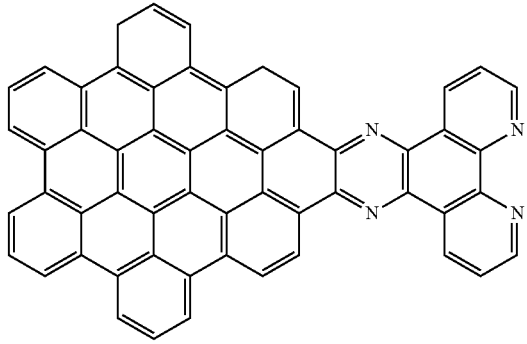

and

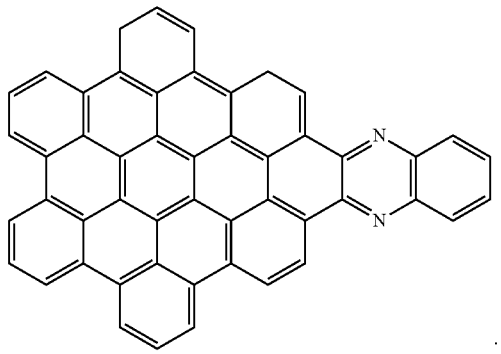

In yet another aspect, a photo-absorbing composition is disclosed, which has a structure from the group consisting of

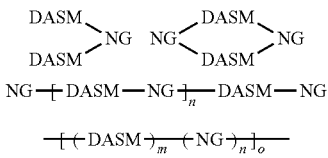

wherein DASM is a small molecule comprising one or more electron donor portions selected from the group consisting of

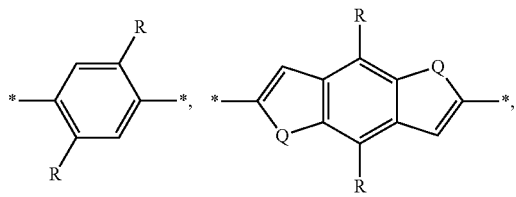

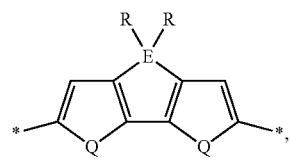

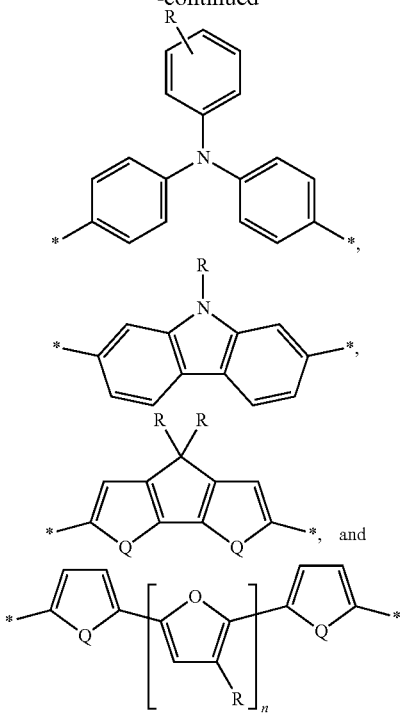

and one or more electron acceptor portions selected from the group consisting of

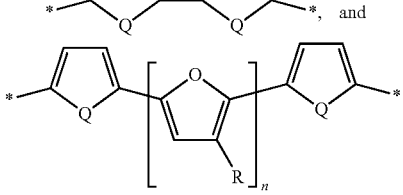

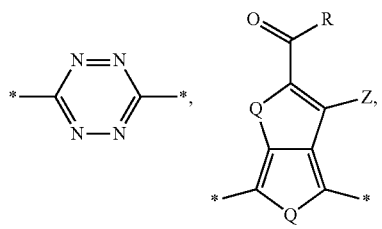

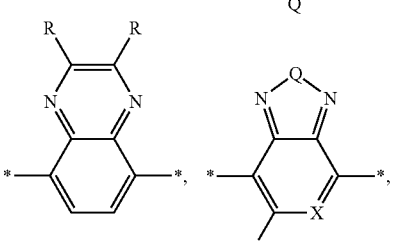

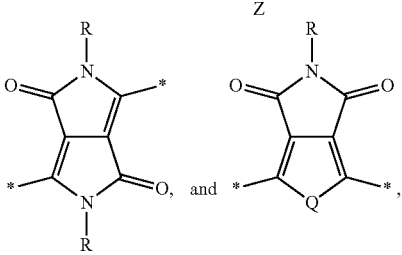

wherein the starred bonds are sites for bonding to other chemical structures; R is, independently in each instance, an alkyl, alkoxy, vinyl, aryl group, or fluorinated hydrocarbon group; Q is, independently in each instance, O, S, or Se; E is, independently in each instance, Si or Ge; Z is, independently in each instance, a proton or a fluorine atom; X is, independently in each instance, C or N; and m, n, and o are integers greater than or equal to 1; and wherein NG is a nanographene structure selected from the group consisting of

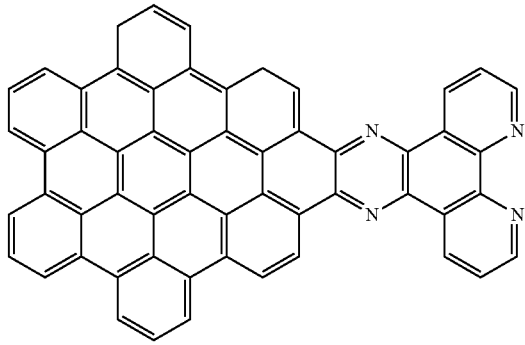

and

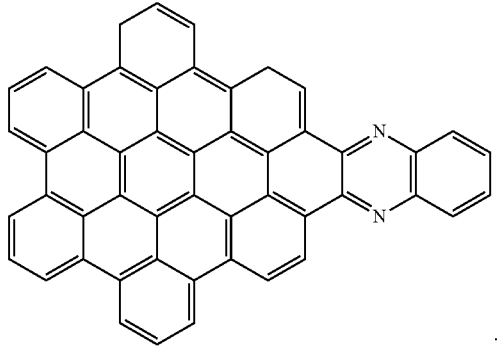

Features and other benefits that characterize embodiments are set forth in the claims annexed hereto and forming a further part hereof. However, for a better understanding of the embodiments, and of the advantages and objectives attained through their use, reference should be made to the accompanying descriptive matter.

DETAILED DESCRIPTION

The present disclosure describes an absorber material for radiation in the solar spectrum, a solar leaf having extended absorption spectrum, and methods and materials of making such a solar leaf. The solar leaf comprises a nanographene-rhenium complex attached to a photo-absorbing small molecule. The photo-absorbing small molecule is a combination of one or more electron-poor donor portions (D) and one or more electron-rich acceptor (A) portions. The photo-absorbing small molecule has an absorption spectrum in the visible range stemming from intermolecular charge transfer between the donor portion and the acceptor portion. The photo-absorbing small molecule can be referred to as a donor-acceptor small molecule (DASM). Donor portions that can be used for a DASM include the following:

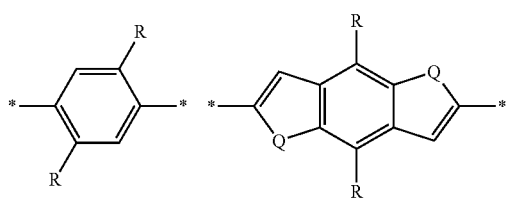

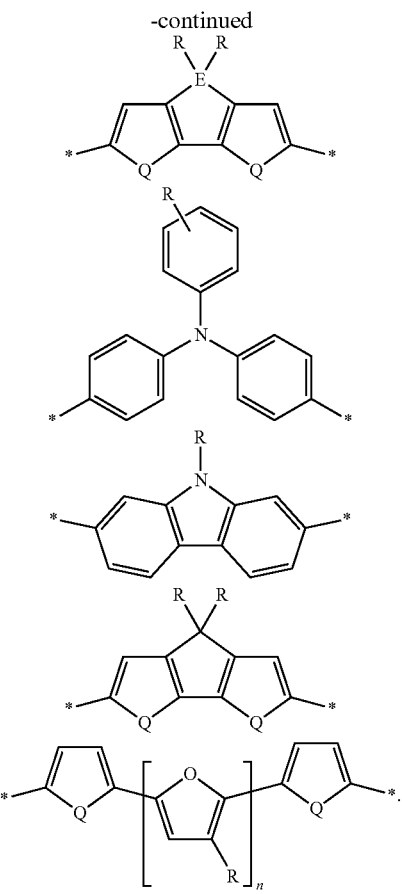

In the structures above, the bonds marked with stars (*) are sites that bond with other chemical structure. In this case these bonds attach to acceptor portions.

Acceptor portions that can be used for a DASM include the following:

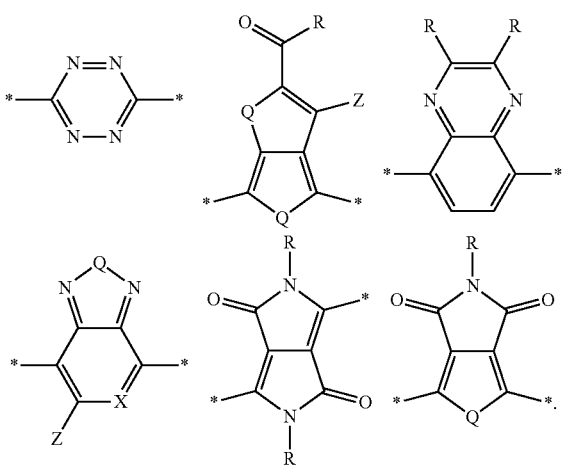

The starred bonds in these structures are sites that bond with other chemical structures. In this case these bonds attach to donor portions such as those listed above. These donor ("D") and acceptor ("A") precursor molecules generally bond to form alternating donor-acceptor structures such as D-A-D, A-D-A, and higher order oligomers D-A-D-A-D, A-D-A-D-A, and so on. This structure can be expressed as

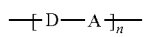

wherein D is an electron-rich donor unit, A is an electron-deficient acceptor unit, and n is an integer between 4 and 200,000. In this application, "DASM" refers to any such molecule or oligomer made of alternating donor and acceptor portions. The R groups in the structures above can be, independently in each instance, alkyl, alkoxy, vinyl, aryl groups, or fluorinated hydrocarbon groups. Q is, independently in each instance, O, S, or Se. E is, independently in each instance, Si or Ge. Z is, independently in each instance, a proton (H or hydrogen atom) or a fluorine atom (F). X is, independently in each instance, C or N.

The D-A structures above can be substantially linear, and/or substantially planar molecules. Alternately, the R groups shown above can be used as branching or cross-linking points. For example, if the R group is vinyl, the vinyl groups can be cross-linked to form a D-A network. In this application, "DASM" also includes such networks. The D-A structures formed by linking the above structures are molecules, so the starred bond sites for terminal donor or acceptor groups will be occupied by protons (hydrogen atoms). The precursors used for making the D-A structures are molecule versions of the structures above, where the starred bond sites are occupied by protons (hydrogen atoms). The reactions for linking the donor portions with the acceptor portions eliminate the hydrogen atoms from the starred bond sites and form bonds between the donor portions and the acceptor portions at the starred bond sites.

These structures can be chemically bonded to the following nanographene absorber structure [1]:

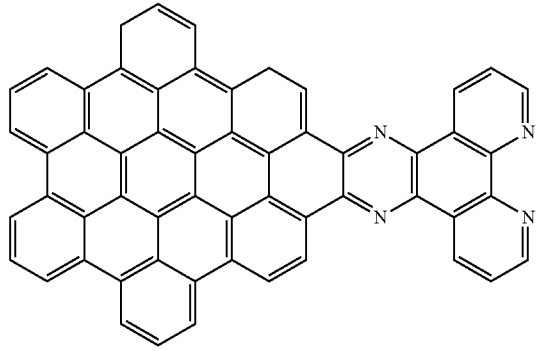

For simplicity, structure [1] will henceforth be referred to as NG. The resulting compounds generally have one of the following structures:

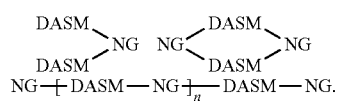

For simplicity, in this disclosure these structures are respectively referred to as "dumbbell," "loop," and "chain" structures.

To make the compounds described above, a precursor of the NG complex is synthesized according to known synthetic scheme (1), below, to yield a polyphenylene-pyrene dione derivative structure [2]:

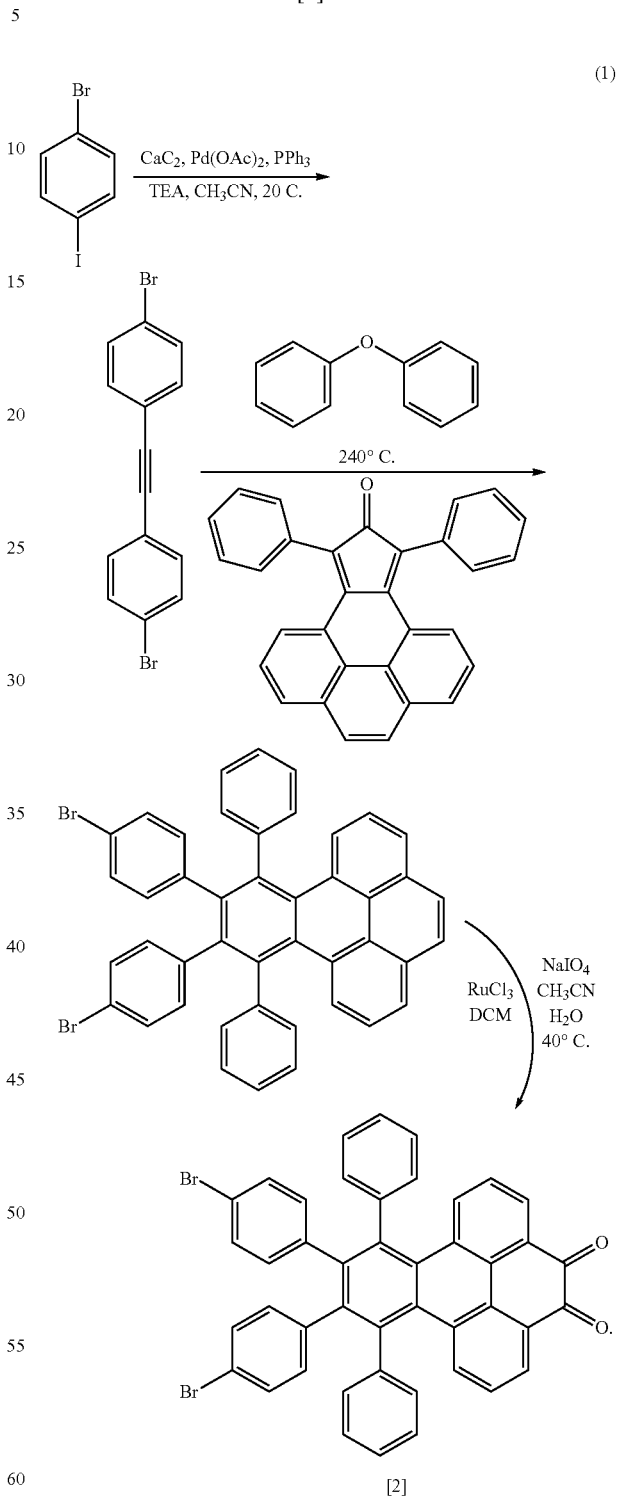

Scheme (1) can start with commercially available 1,2-bis-(4-bromophenyl)ethyne, or the ethyne can be synthesized from 1-bromo-4-iodobenzene in a mixture of calcium carbide (or acetylene gas), palladium acetate, triphenylphosphine, triethylamine, and cyanomethane at 20° C. The ethyne is mixed with 9,11-diphenyl-10H-cyclopenta[e]pyren-10-one in diphenyl ether and allowed to react at 240° C. for 1-2 hours. The polyphenylene-pyrene intermediate 10,11-bis(4-bromoophenyl)-9,12-diphenylbenzo[e]pyrene can be isolated by cold precipitation and filtering. The polyphenylene-pyrene intermediate is dissolved in dichloromethane (DCM), and to the solution is added a solution of sodium iodate (e.g. 4M) in water followed by ruthenium chloride hydrate in cyanomethane solution. The mixture is stirred at 40° C. for one day before quenching with water. Polyphenylene-pyrene dione structure [2], 10,11-bis-(4-bromophenyl)-9,12-diphenylbenzo[e]pyrene-4,5-dione, can be isolated from the organic phase by DCM extraction followed by concentration under reduced pressure and silica gel column chromatography to yield dione structure [2]. For simplicity, structure [2] above will henceforth be referred to in text as PH—Br$_2$, where PH denotes the divalent polyphenylene-pyrene dione portion of structure [2].

Structure [2] above can be coupled to DASM structures by forming trialkyl tin terminated derivatives of the DASM structures. DASMs with thiophene end groups can be brominated by reaction with NBS in appropriate solvent to make (DASM)-(Br)$_x$. The bromine atoms attach to the thiophene groups at a position alpha to the thiophene sulfur atom. If the DASM is not originally thiophene terminated, the DASM can be brominated, and the brominated DASM then cross-coupled using dithiophene Stille reagents, using the trimethylstannate version as an example, under normal Stille coupling conditions, as follows:

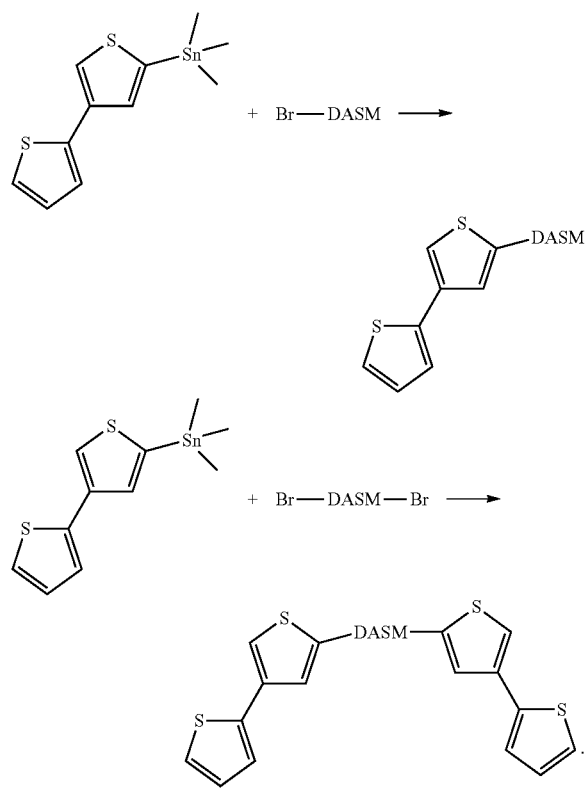

D-terminated DASMs can be brominated by reaction with NBS. A-terminated DASMs can be brominated using NBS in a polar aprotic solvent such as dimethylformamide (DMF), optionally mixed with chloroform or tetrahydrofuran (THF), or using a mixture of quinoxoline and benzothiadiazole bromine in acetic acid. If the two resulting structures above are referred to in text as DASM-Th and DASM-(Th$_2$), the brominated species would be DASM-Th—Br and DASM-(ThBr)$_2$.

Trialkyl tin groups can then be added, replacing the Br atoms by nucleophilic substitution. Scheme (2) illustrates:

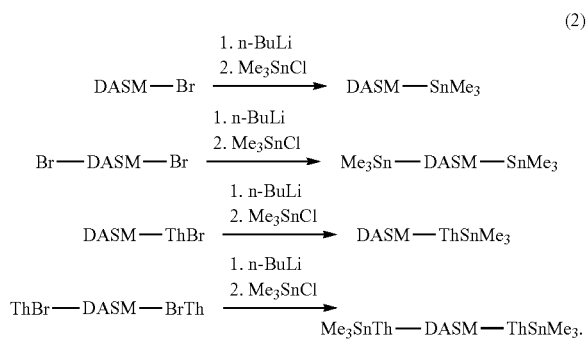

The brominated DASM is converted into a Stille terminated DASM that can be coupled to a bromine-terminated molecule in a subsequent reaction. The brominated, thiophene-terminated DASMs can likewise be converted into a Stille terminated, thiophenated DASM. The Stille structures resulting from scheme (2) above are then reacted with the brominated structure [2] above to complete the coupling, as follows:

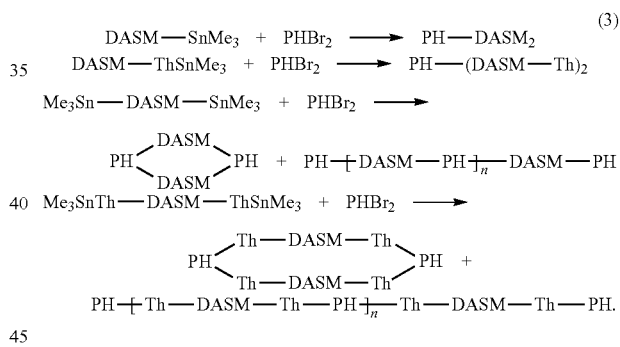

The polyphenylene-pyrene dione structure PH is then condensed and reacted with 1,10-phenanthroline diamine under pyridine reflux to form a precursor of the nanographene complex NG, according to the general scheme

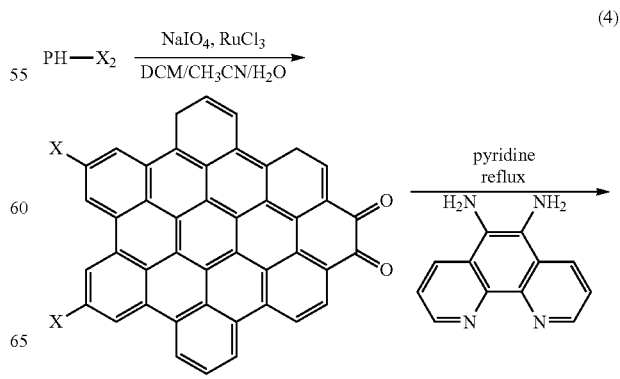

The PH—$X_2$ polyphenylene-pyrene dione structure condenses to form an NG-dione precursor structure. The NG-dione precursor is converted to an NG structure by reacting with a suitable diamine, such as the phenanthroline diamine example above. Thus, the structure resulting from scheme (3) above are converted to DASM-nanographene complex structures, according to general scheme (4), as follows:

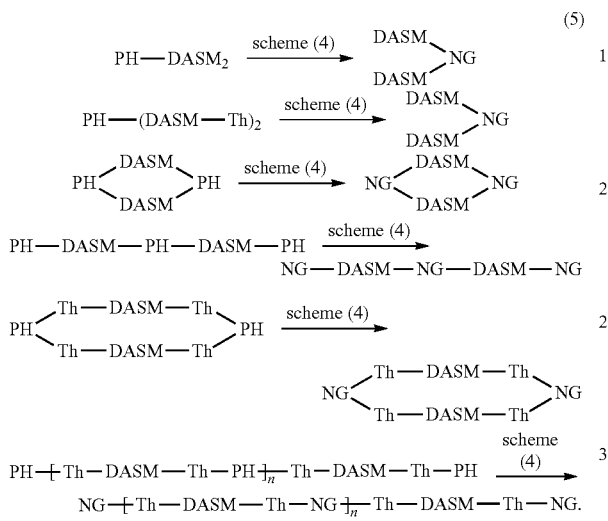

(5)

Alternately, the PH precursor can be condensed to an NG precursor using the reactions of scheme (4) prior to reaction with a Stille-terminated DASM according to scheme (3). In such cases, the reactions of scheme (3) would be performed using an $NGBr_2$ precursor, rather than a $PHBr_2$ precursor. While the above reaction schemes are depicted as using a Stille coupling reaction, it should be noted that the same C—C bonds can be formed, as known in the art, using Suzuki cross-coupling reactions and C—H activation cross-coupling reactions.

The structures resulting from scheme (5) represent solar leaf materials that can be formed into films comprising nanographene light-absorber materials and light-absorbing donor-acceptor small molecules. The films have absorption spectra broader than that of the nanographene or donor-acceptor materials alone. The materials can be formed into films by dissolving them in an appropriate solvent, applying the solution to a surface, and removing the solvent. A binder material, such as a thermoplastic polymer material, can be added in some cases to facilitate handling the film, if necessary. In other cases, the extended solar leaf material is a polymer that can be extruded onto a surface or blown into a film.

It should be noted that, in the event a cross-linked DASM network is used as the starting point for any of the reactions above, articulated structures having multiple branches of DASM-NG linkages and loops can result. For example, if a DASM has the structure $$\begin{array}{c} A-D-A \\ | \\ A-D-A \end{array}$$

where the donor molecules are cross-linked by a vinyl group, each acceptor portion can be bonded to an NG group, as follows:

$$\begin{array}{c}
NG\diagdown \quad \diagup NG \qquad \diagup NG \\
\quad A-D-A \qquad A-D-A \\
\qquad \qquad NG\diagdown \\
\quad A-D-A \qquad A-D-A \\
NG\diagup \quad \diagdown NG \qquad \diagdown NG \\
\qquad \qquad A-D-A \\
\qquad NG\diagdown \quad | \quad \diagup NG \\
\qquad \quad A-D-A \\
\qquad \qquad NG \\
\\
NG\diagdown \qquad \qquad A-D-A \\
\quad A-D-A-NG-A-D-A\diagdown \\
\qquad \qquad \qquad \qquad \qquad NG. \\
\quad A-D-A \\
NG \qquad NG
\end{array}$$

While cross-linking is shown above between two donor portions (where R is a vinyl group, for example), cross-linking may occur between two acceptor portions and/or between donor and acceptor portions, so long as a cross-linkable group is included in one or more donor or acceptor groups. The structures above illustrate that cross-linking of DA structures can lead to networked solar leaf structures that mix nanographene absorber structures with DA absorber structures in extended matrices. The absorption spectrum of such matrices can be tailored by selecting the content and type of absorbers and donors used. In this way, a photo-absorbing composition can be made having the general structure $$-[(DASM)_m(NG)_n]_o-,$$

where DASM and NG are defined as above, and m, n, and o are integers greater than or equal to 1. This structure is a polymer network of DASM and NG groups, which can have any proportion of DASM to NG groups, and may be random, pseudo-random (appearing random at one scale and non-random at another scale), pseudo-block (appearing block at one scale and non-block at another scale), or block.

Another nanographene structure that can be used in place of structure [1] (i.e. as the "NG" group for all the structures and schemes herein) is as follows:

[3]

Structure [3] is made in a reaction scheme similar to scheme (4) using 1,2-benzenediamine in place of the phenanthroline diamine reagent. Other aromatic and polyaromatic ortho-diamines can also be used in the same scheme. Mixtures of different types of NG groups can be used in one photo-absorbing composition, in different molecules and in the same molecule.

An exemplary synthesis using the dithienosilole donor and the thiadiazole acceptor in an ADA format small molecule follows:

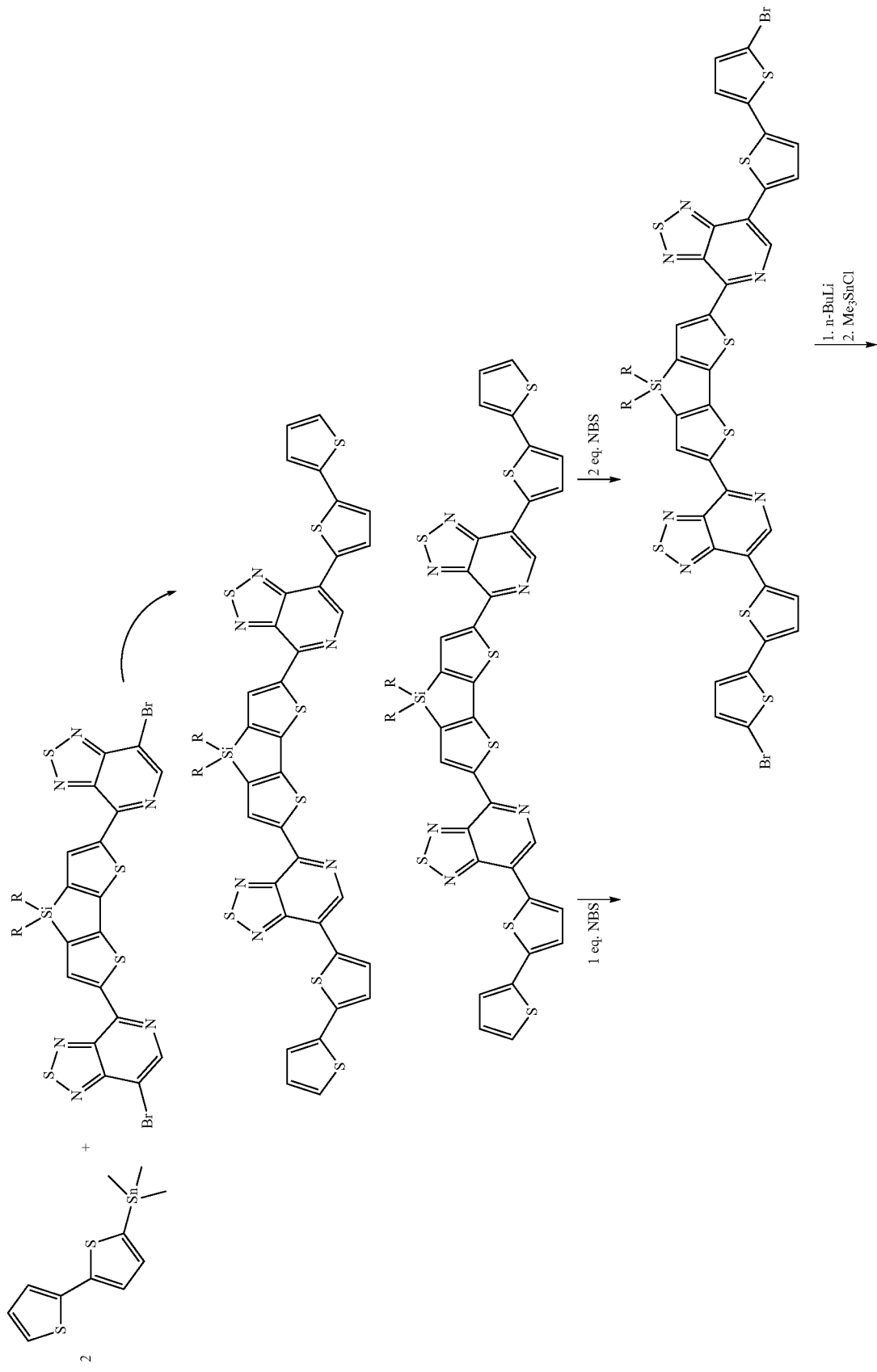

-continued
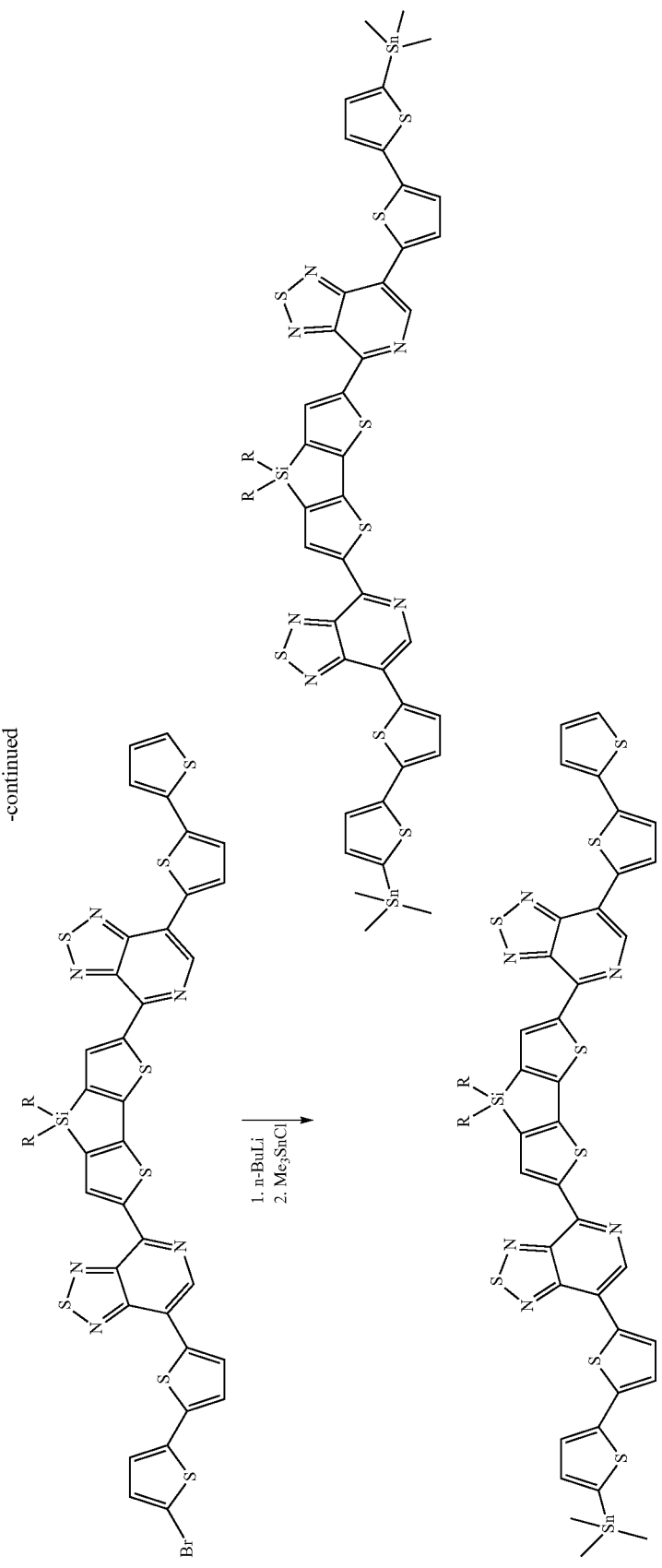

For the monovalent-functionalized DASM above, the final step is as follows:
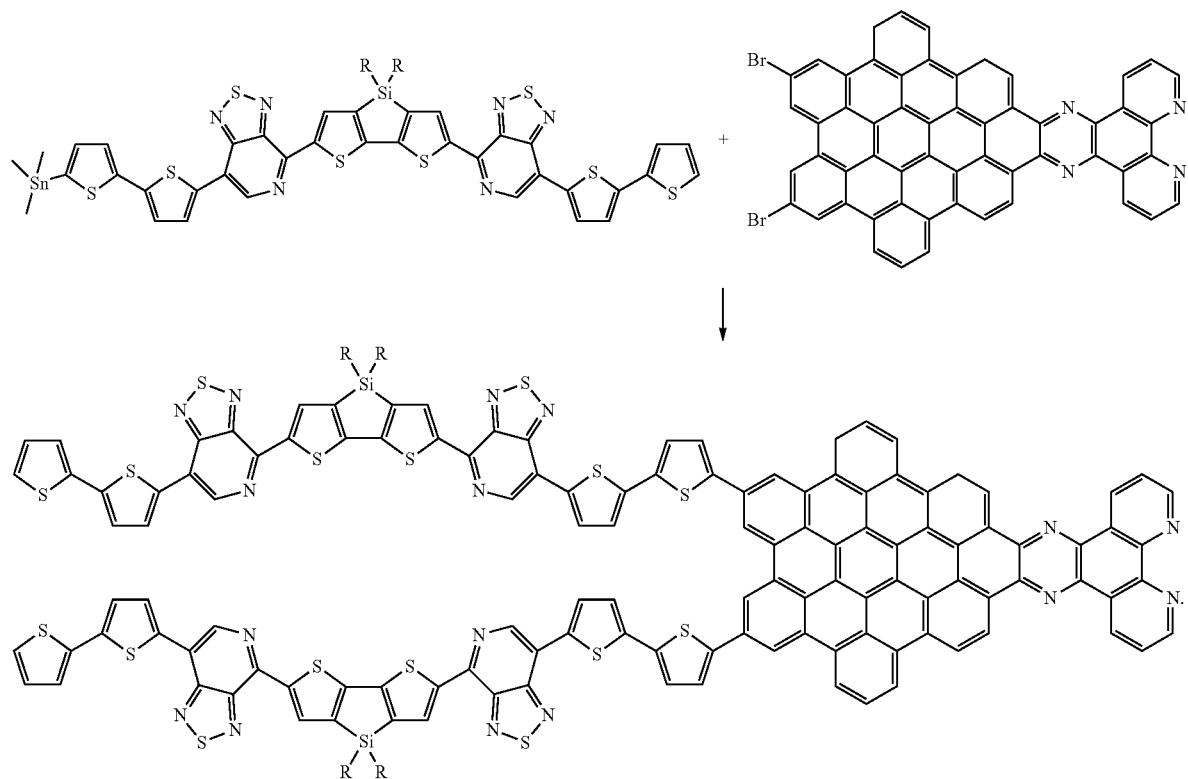
For the divalent-functionalized DASM above, one example product of the final step in the synthesis is as follows:

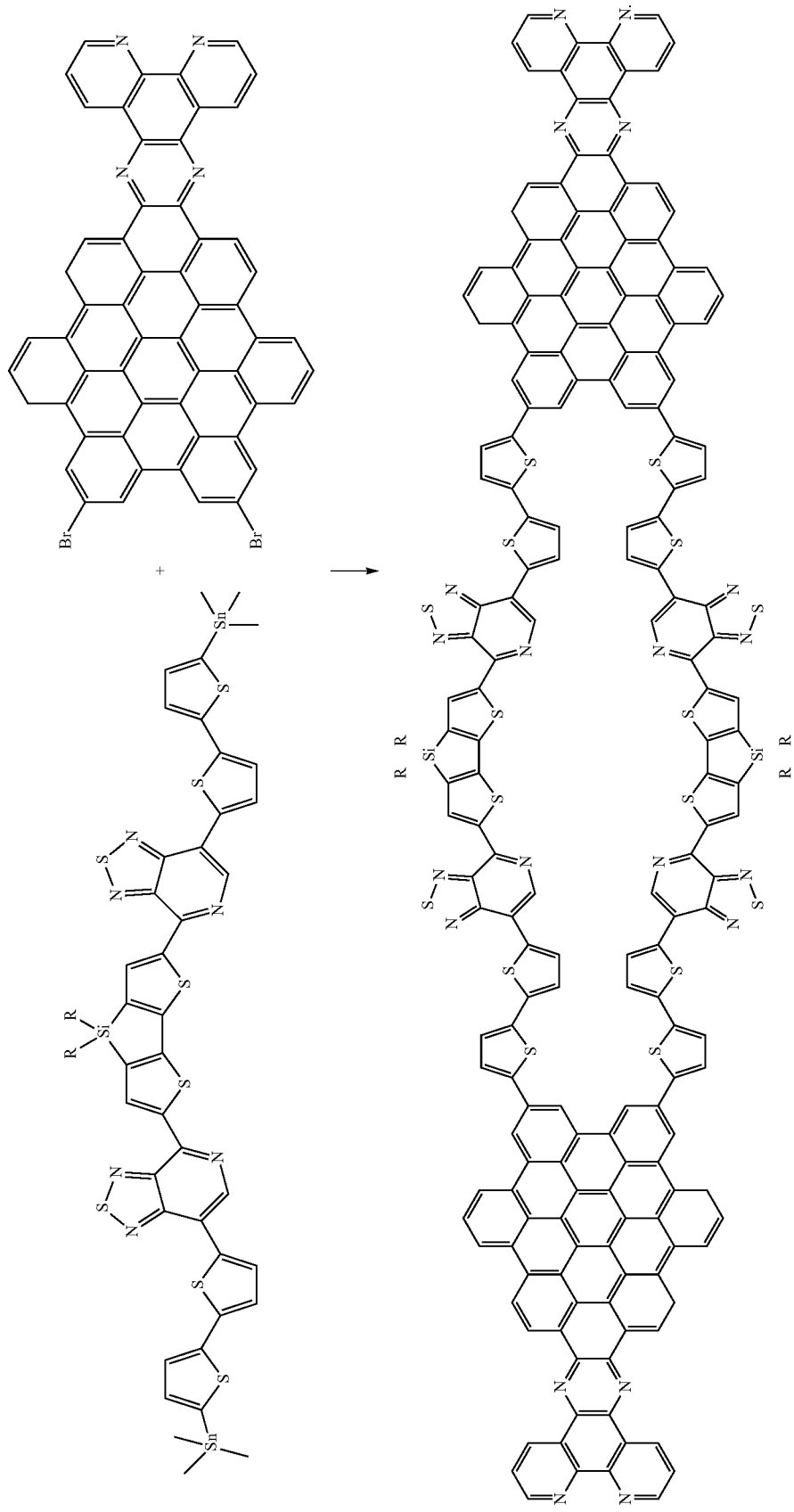

Other products are -DASM-NG- chains. Another exemplary synthesis, using an A—D—A structure with the tetrazine acceptor and the substituted benzene donor, is as follows:
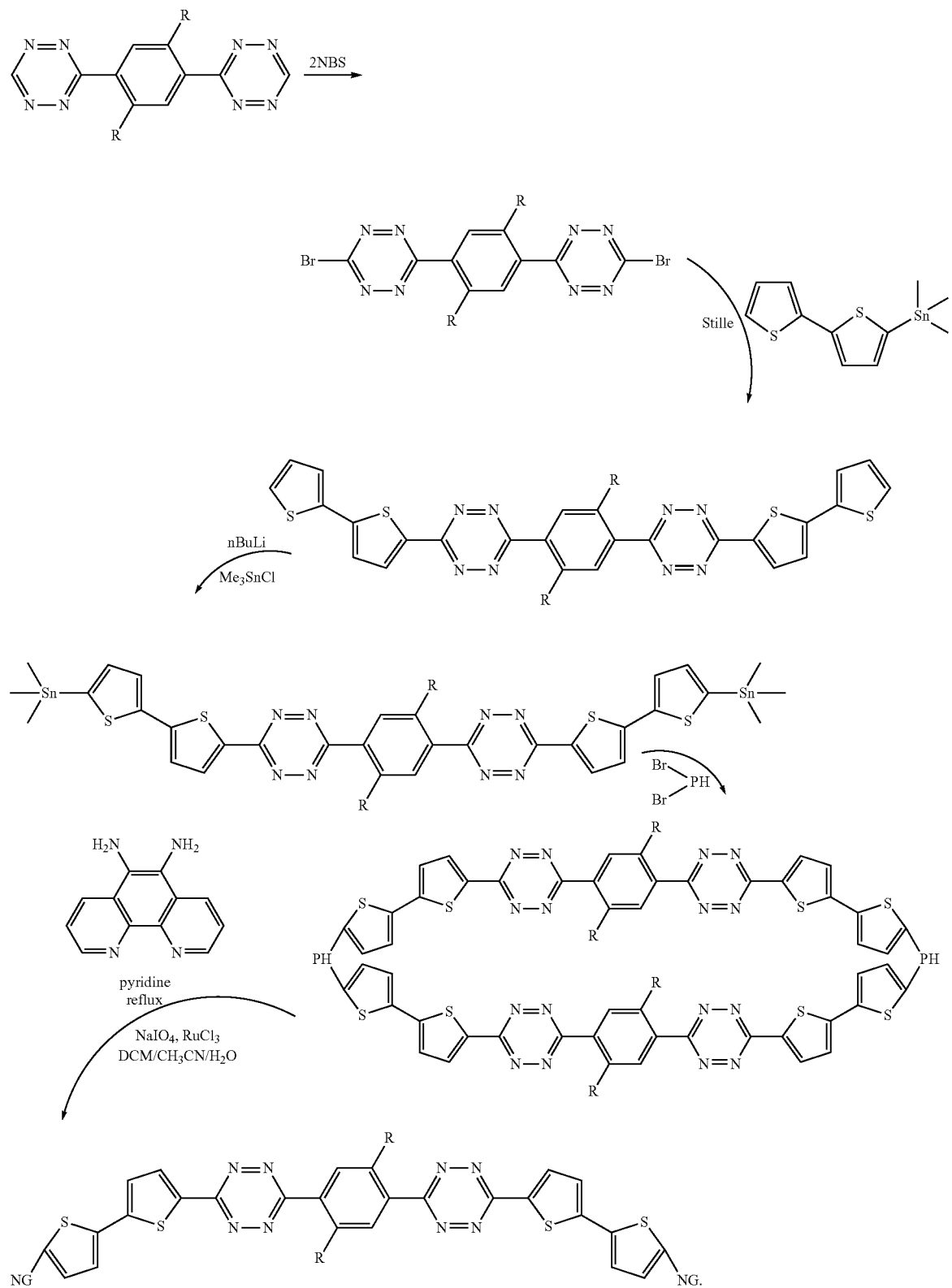

For simplicity of drawings, the loop structure

is shown as the product, but it should be understood that chain structures, as described herein, will also be made in this synthesis, and that dumbbell structures can be made by starting with less NBS in the initial bromination step to yield mono-brominated species of the DASM. It should also be noted that mixtures of the loop, chain, and dumbbell structures can be obtained using mixtures of mono- and di-brominated species. It should also be noted that, if the R groups are vinyl groups, the DASM can be cross-linked, as described above, prior to performing the synthesis above, to yield the polymer network structure

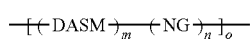

described above.

The photo-absorbing compositions described herein can be formed into a solar leaf by forming a film from the photo-absorbing composition, or including the photo-absorbing composition. In general, these compositions can be formed into a film by dissolving or suspending any of the compositions described above in a suitable solvent, such as dichloromethane, THF, chloroform, benzene, toluene, dioxane, chlorobenzene, dichlorobenzene, DMF, xylenes, or mixtures thereof, to form a solution, applying the solution to a surface, and removing the solvent by low-temperature evaporation (for example under vacuum or other evaporating atmosphere) to form a film on the surface. Process aids such as chloronaphthalene, diiodooctane, or 1,8-octanedithiol can be used in amount of 5-10% or less to promote formation of high-quality films. Solvent removal can also be performed at ambient conditions for slower film crystallization to promote a more ordered film structure. If the surface is a solid, such as a glass plate, the film can be peeled off the surface. Alternatively, the film may be formed on a liquid surface, such as an aqueous pool, and the resulting film can be easily lifted from the aqueous surface. Finally, films can be formed by spin-coating, doctor blading, or ink jet printing.

The previous description of the disclosed embodiments is provided to enable any person skilled in the art to make or use the disclosed embodiments. Various modifications to these embodiments will be readily apparent to those skilled in the art, and the generic principles defined herein may be applied to other embodiments without departing from the scope of the disclosure. Thus, the present disclosure is not intended to be limited to the embodiments shown herein, but is to be accorded the widest scope possible consistent with the principles and features as defined by the following claims.

The invention claimed is:
1. A method of making a photo-absorbing composition, comprising:
forming a donor-acceptor small molecule (DASM) by bonding an electron donor portion selected from the group consisting of

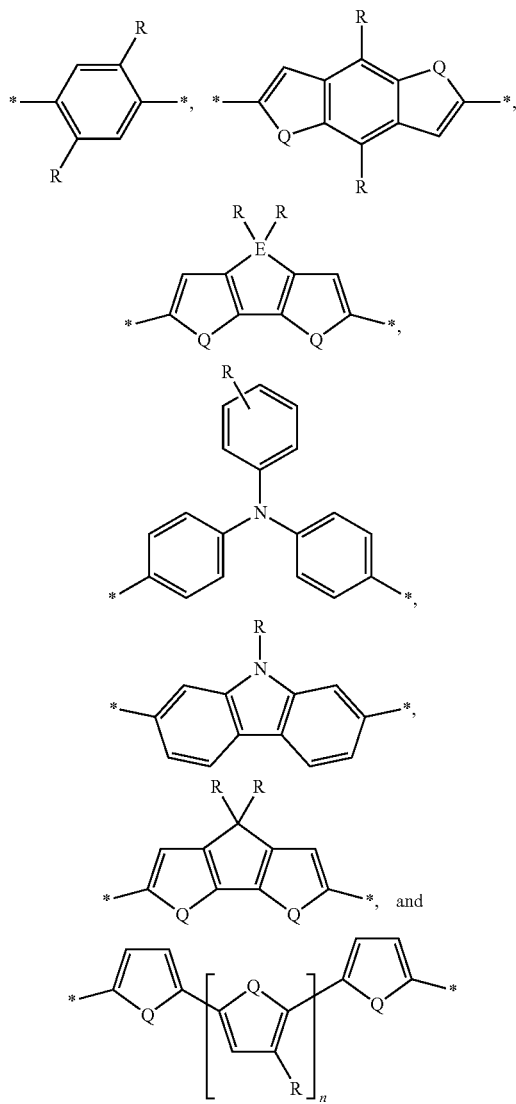

to an electron acceptor portion selected from the group consisting of

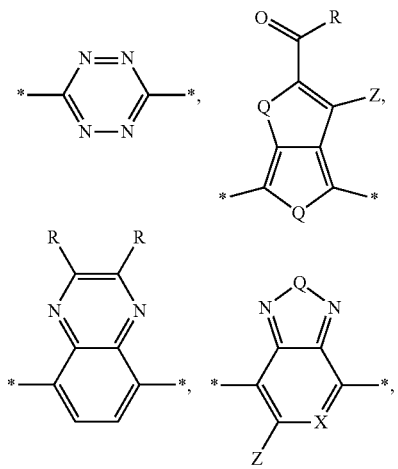

-continued

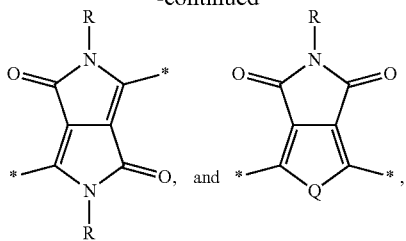

wherein:
the starred bonds are sites for bonding to other chemical structures;
R is, independently in each instance, an alkyl, alkoxy, vinyl, aryl group, or fluorinated hydrocarbon group;
Q is, independently in each instance, O, S, or Se;
E is, independently in each instance, Si or Ge;
Z is, independently in each instance, a proton or a fluorine atom;
X is, independently in each instance, C or N; and
n of the electron donor portion is an integer greater than or equal to 1; and
bonding the DASM to a nanographene structure using a Stille coupling reaction, a Suzuki cross-coupling reaction, or a C—H activation cross-coupling reaction, the nanographene structure (NG) selected from the group consisting of

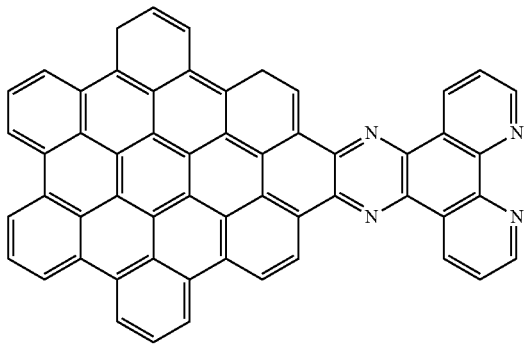

and

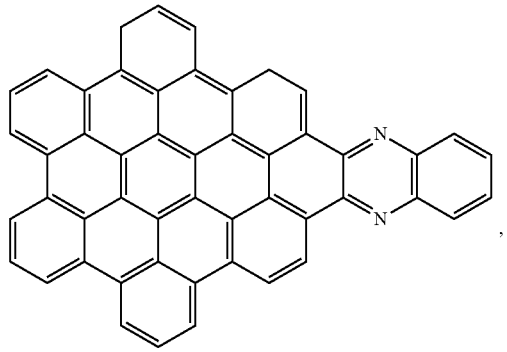

the photo-absorbing composition having a general structure selected from the group consisting of

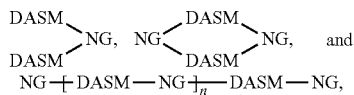

wherein, n of the photo-absorbing composition is an integer greater than or equal to 1.

2. The method of claim 1, wherein bonding the DASM to the nanographene structure comprises:
forming a Stille reagent from the DASM;
brominating a polyphenylene-pyrene dione precursor of the nanographene structure to form a brominated polyphenylene-pyrene dione precursor of the nanographene structure; and
reacting the Stille reagent with the brominated polyphenylene-pyrene dione precursor of the nanographene structure in a Stille coupling reaction.

3. The method of claim 2, wherein forming the DASM comprises cross-linking two donor portions of the DASM, cross-linking two acceptor portions of the DASM, and/or cross-linking a donor portion and an acceptor portion of the DASM.

4. The method of claim 2, wherein the DASM has more than one electron donor portion or more than one electron acceptor portion.

5. The method of claim 2, wherein bonding the DASM to the nanographene structure comprises forming a polymer network of the DASM and the nanographene structure.

6. The method of claim 2, wherein forming the Stille reagent comprises adding a thiophene group to the DASM.

7. The method of claim 2, wherein reacting the Stille reagent with the brominated polyphenylene-pyrene dione precursor forms a DASM-nanographene dione precursor, and the method further comprises condensing the DASM-nanographene dione precursor and forming a DASM-nanographene complex.

8. The method of claim 7, wherein forming the DASM-nanographene complex comprises forming a DASM-nanographene dione precursor and reacting the DASM-nanographene dione precursor with a diamine selected from the group consisting of 1,2-benzenediamine and 1,10-phenanthroline diamine.

9. A method of making a photo-absorbing composition, comprising:
forming a donor-acceptor small molecule (DASM) by bonding an electron donor portion selected from the group consisting of

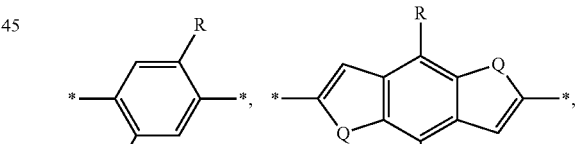

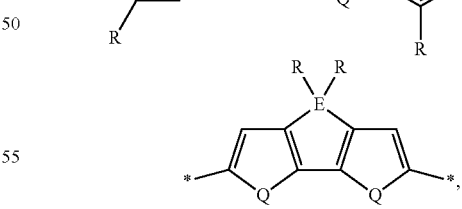

-continued

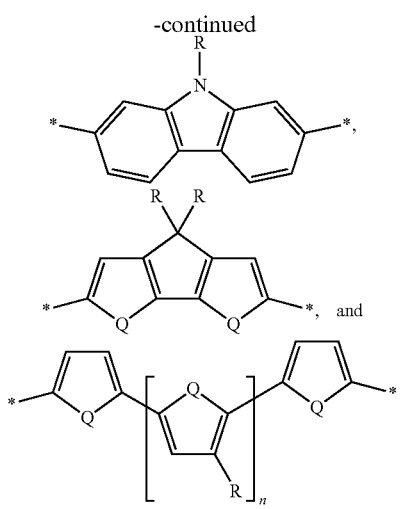

to an electron acceptor portion selected from the group consisting of

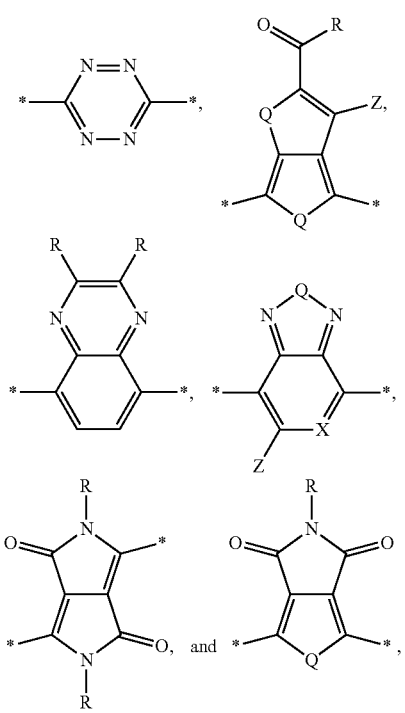

wherein:
the starred bonds are sites for bonding to other chemical structures;
R is, independently in each instance, an alkyl, alkoxy, vinyl, aryl group, or fluorinated hydrocarbon group;
Q is, independently in each instance, O, S, or Se;
E is, independently in each instance, Si or Ge;
Z is, independently in each instance, a proton or a fluorine atom;
X is, independently in each instance, C or N; and
n of the electron donor portion is an integer greater than or equal to 1; and
bonding the DASM to a nanographene structure using a Stille coupling reaction, a Suzuki cross-coupling reaction, or a C—H activation cross-coupling reaction, the nanographene structure (NG) selected from the group consisting of

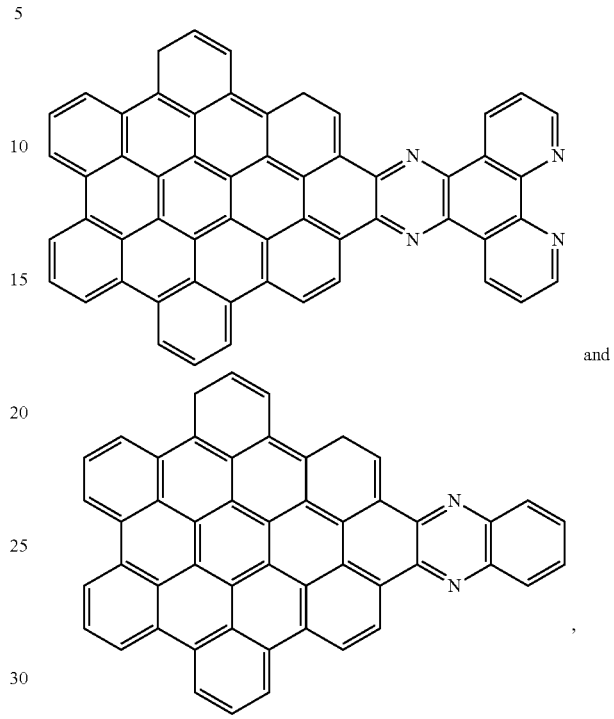

and the photo-absorbing composition having a general structure selected from the group consisting of

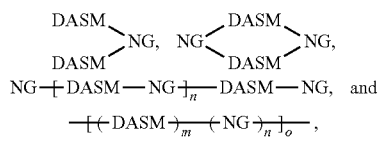

wherein m, n, and o of the photo-absorbing composition are integers greater than or equal to 1.

10. The method of claim 9, wherein bonding the DASM to the nanographene structure comprises:
forming a Stille reagent from the DASM;
brominating a polyphenylene-pyrene dione precursor of the nanographene structure to form a brominated polyphenylene-pyrene dione precursor of the nanographene structure; and
reacting the Stille reagent with the brominated polyphenylene-pyrene dione precursor of the nanographene structure in a Stille coupling reaction.

11. The method of claim 10, wherein forming the DASM comprises cross-linking two donor portions of the DASM, cross-linking two acceptor portions of the DASM, and/or cross-linking a donor portion and an acceptor portion of the DASM.

12. The method of claim 10, wherein the DASM has more than one electron donor portion or more than one electron acceptor portion.

13. The method of claim 10, wherein bonding the DASM to the nanographene structure comprises forming a polymer network of the DASM and the nanographene structure.

14. The method of claim 10, wherein reacting the Stille reagent with the brominated polyphenylene-pyrene dione precursor forms a DASM-nanographene dione precursor, and the method further comprises condensing the DASM-nanographene dione precursor and forming a DASM-nanographene complex.

15. The method of claim 14, wherein forming the DASM-nanographene complex comprises forming a DASM-nanographene dione precursor and reacting the DASM-nanographene dione precursor with a diamine selected from the group consisting of 1,2-benzenediamine and 1,10-phenanthroline diamine.

16. The method of claim 10, wherein forming the Stille reagent comprises adding a thiophene group to the DASM.

\* \* \* \* \*